United States Patent [19]

Blackmore

[11] Patent Number: 4,585,456
[45] Date of Patent: Apr. 29, 1986

[54] CORRECTIVE LENS FOR THE NATURAL LENS OF THE EYE

[75] Inventor: John M. Blackmore, Redwood City, Calif.

[73] Assignee: Ioptex Inc., Azusa, Calif.

[21] Appl. No.: 588,579

[22] Filed: Mar. 12, 1984

[51] Int. Cl.$^4$ .............................................. A61F 2/16
[52] U.S. Cl. ........................................................ 623/6
[58] Field of Search ........................................... 3/13, 1

[56] References Cited

U.S. PATENT DOCUMENTS

| | | | |
|---|---|---|---|
| 2,834,023 | 5/1958 | Lieb | 3/13 X |
| 4,244,060 | 1/1981 | Hoffer | 3/13 |
| 4,424,597 | 1/1984 | Schlegel | 3/13 |

FOREIGN PATENT DOCUMENTS

| | | | |
|---|---|---|---|
| 2124500 | 2/1984 | United Kingdom | 3/13 |

Primary Examiner—Ronald L. Frinks
Attorney, Agent, or Firm—Bielen & Peterson

[57] ABSTRACT

A corrective lens for the in-tact natural lens of the eye which utilizes an optical body formed of a material which is compatable with the tissue of the eye. The optical body is positioned against the natural lens of the eye and is held in place immediately adjacent the natural lens of the eye.

8 Claims, 5 Drawing Figures

CORRECTIVE LENS FOR THE NATURAL LENS OF THE EYE

BACKGROUND OF THE INVENTION

The present invention relates to a novel and useful corrective lens for the natural lens of the eye.

Correction of eyesight deficiencies such as myopia, hyperopia, astigmatism and the like have employed the use of lenses which are temporarily mounted in a pair of glasses or contact lenses, the latter being placed on the outer surface of the cornea of the eye. These systems of correction of visual defects are temporary in that the glasses or lenses must be placed and removed during a certain period of time or during certain activities, e.g. while sleeping, swimming, and the like.

Permanent correction of these conditions have been attempted by the performance of kerato-refractive surgery. These surgical techniques include keratomeleusis in which the corneal layer is removed, reshaped, and replaced. Also, radial keratatomy surgery has been used where a multiplicity of cuts into the cornea layer are made to adjust the curvature of the cornea with subsequent healing. These kerato-refractive surgical techniques are not reversible and can result in permanent damage to the structure of the eye if they are not successful.

Intraocular lenses have also been used to solve this problem but they are generally designed to correct for aphakia after cataract removal.

A permanent device for correcting visual defects which is reversible in effect would be a great advance in the field of eye care.

SUMMARY OF THE INVENTION

In accordance with the present invention a novel and useful corrective lens in use in conjunction with the in-tact natural lens of the eye is provided.

The corrective lens of the present invention employs an optical body formed of material which is intended to be bio-compatable with the eye. The optical body may be defined as a flexible resilient object capable being folded in half and returning to its original shape. Of course, the optical body would be capable of refracting light to correct the visual acuity of the eye containing the subject in-tact natural lens.

The invention further includes means for positioning the optical body within the eye adjacent the in-tact natural lens thereof. Such means may externalize in forming said optical body with a side which conforms to the shape of the in-tact natural lens such that the optical body may be placed on the outer surface of the natural lens. In such a case the optical body would adhere to the natural lens. In addition, at least one appendage may be connected to the optical body or extension of the same toward the periphral portions of the eye for contact with the same. Such an appendage may take the form of an open loop, closed loop, or any other appendage configuration known in the art with respect to intraocular lenses. The appendage may also be constructed of flexible material. In certain cases it may be advantageous to form any of the appendages connected to the optical body of material possessing a rigidity greater than the optical body itself. Where the appendage is formed of a flexible material, reinforcing elements may be employed to provide this rigidity.

Moreover, the corrective lens of the present invention may be constructed using a haptic which connects the optical body and to the at least one appendage connected to the optical body. The haptic would permit the user to easily handle and manipulate the corrective lens during the process of insertion within the eye.

It may be apparent that a novel and useful corrective lens for the in-tact natural lens within the eye is provided.

It is therefore an object of the present invention to provide a corrective lens for the in-tact natural lens of the eye which permanently corrects for visual defects.

It is another object of the present invention to provide a corrective lens for the in-tact natural lens of the eye which does not damage the cornea or other structure of the eye during and after insertion of the same within the eye.

It is yet another object of the present invention to provide a corrective lens for the in-tact natural lens of the eye which may be easily removed and/or replaced with another corrective lens as desired.

Another object of the present invention is to provide a corrective natural lens of the eye which may be employed to correct relatively minor visual defects and may be used cosmetically.

It is another object of the present invention to provide a corrective lens for the in-tact natural lens within the eye which has a greater range of correction than prior kerato-fractive techniques.

The invention possess other objects and advantages especially as concerns particular characteristic and features thereof which will become apparent as the specification continues.

For a better understanding of the invention is made to the hereinafter description of the preferred embodiments which should be taken in conjunction with the hereinabove described drawings.

DESCRIPTION OF THE PREFERRED EMBODIMENTS

Various aspects of the present invention will evolve from the following detailed description thereof which should be referenced to the hereinabove described drawings.

Figure 1:
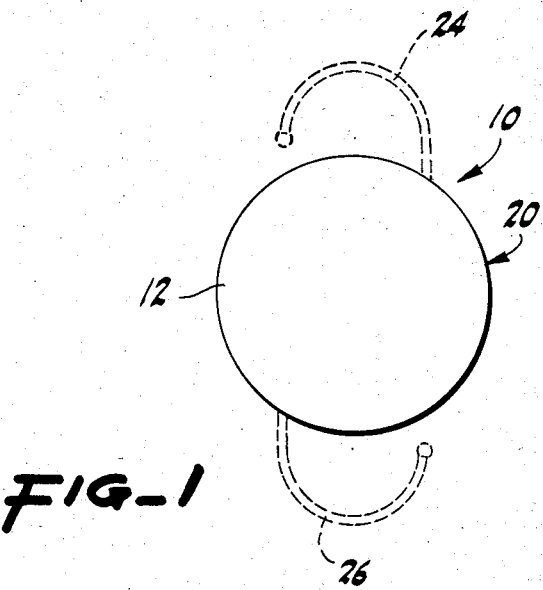
FIG. 1 is a top plan view of an embodiment of the present invention.

The invention as a whole shown in the drawings by reference character 10, 10A and 10B. Turning to FIG. 1 it may be seen that an optical body 12 may be formed of bio-compatable material in relation to the tissue within the eye. For example, polymethylmethacrylate, PMMA, silicone rubber, polyhydroxyethyl methocrylate (HEMA), the copolymer of silicone and methylmethacrylate, polyvinylpyrrolidone (PVP), and other known materials which are bio-compatable and preferably hydrophilic and/or permeable to oxygen. Optical body 12 may include a concave surface 14, FIG. 2, which generally conforms to the convex surface 16 of the natural lens 18. Surface 14 would constitute means 20 for positioning optical body 12 within eye 22 adjacent the in-tact natural lens 18 thereof.

Returning to FIG. 1 it may be seen that means 20 may also take form of including appendages 24 and 26 which are in the form of open loop members (shown in phantom FIG. 1). Any appendage configuration may be usable in this regard such as plate-like structures, open loops, closed loops, structures which penetrate or otherwise hold on to the eye tissue and the like.

Returning to FIG. 2 it may be seen that eye 22 is illustrated showing the cornea 28, iris 29, and pupil 32. Lens 10A is shown in place such that surface 14 of optical body 12 is placed against surface 16 of the in-tact natural lens 18 without deforming the latter. Means 20 including appendages 24 and 26 (not shown in phantom) holds lens device 10A in place along the optical axis of eye 22 directly beneath pupil 32. Appendages 24 and 26 are shown contacting the peripheral portion of the eye, specifically at the ciliary sulcus 30. Appendages 24 and 26 and optical body 12 may be molded into one piece to facilitate manufacture of lens device 10.

Figure 2:
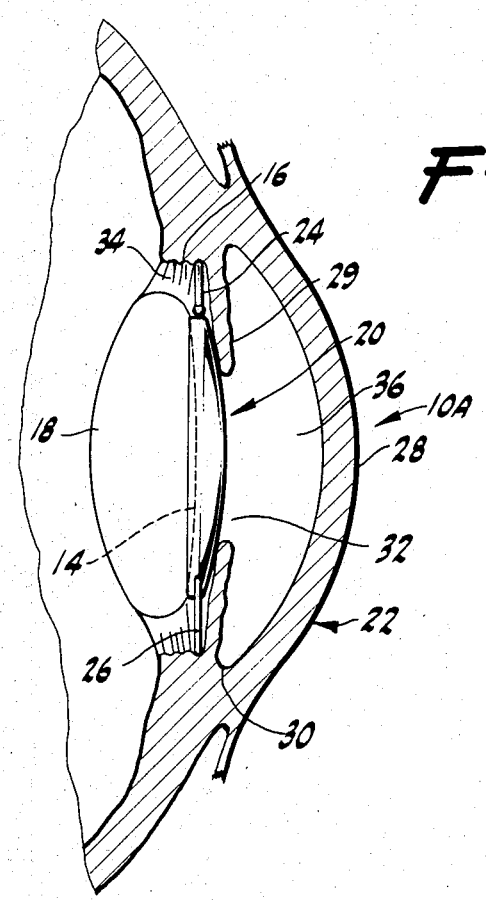
FIG. 2 is a sectional view of the embodiment in FIG. 1 within an eye.

Device 10 is shown in FIG. 2 as being placed within the posterior chamber 34 of eye 22. It is anticipated that lens 10 may also be placed with a portion or all of the same in the anterior chamber 36 of eye 22.

Figure 4:
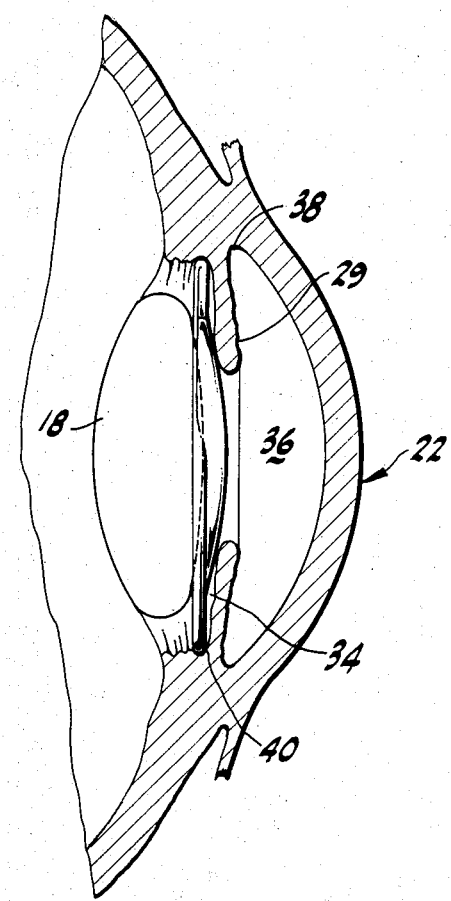
FIG. 4 is a sectional view showing the embodiment of FIG. 3 within an eye.
Figure 3:
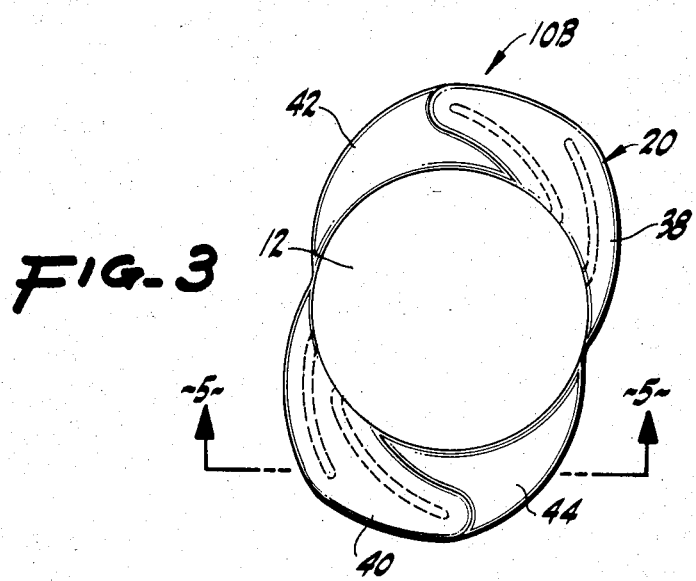
FIG. 3 is a top plan view of another embodiment of the present invention.
Figure 5:
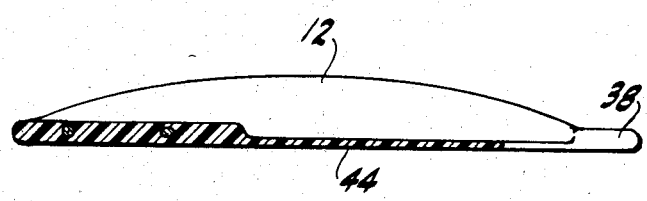
FIG. 5 is a view taken along 5—5 of FIG. 3.

Turning to FIGS. 3-5 it may be seen that another embodiment 10B of the lens 10 has been depicted. Optical body 12 includes means 20 for positioning the same within eye 22 which includes appendages 38 and 40. Appendages 38 and 40, FIG. 5, would be predetermined to be more rigid than optical body 12, although appendages 38 and 40 would still be constructed of a flexible material, preferably having a memory. Haptic structures 42 and 44 aid in the fixation of appendages 38 and 40, which will be hereinafter described, and also facilitate the handling of lens 10B, FIG. 3. Moreover, appendages 38 and 40 in combination with haptic structures 42 and 44 inhibit incapsulation of any portion of lens 10 by natural tissue. Again, the embodiment shown in FIG. 3 may be molded into one piece and may contain appendages 38 and 40 which are simply manufactured of material which is more rigid than optical body 12.

With reference to FIG. 4 it may be seen that lens 10 as depicted in FIG. 3 is placed in essentially the same position within eye 22 as the embodiments of lens 10 shown in FIG. 1.

In operation, the surgeon would select corrective lens 10 having the proper corrective optics for the particular eye 22. A limbal cut perhaps as small as 3 to 4 millimeters, would be made. Lens 10 would be inserted into the anterior chamber 36 of eye 22, through pupil 32 to the posterior chamber 34 of eye 22 as shown in FIGS. 2 and 4. If the lens 10 included appendages such as appendages 24 and 19 or 38 and 40 they would be very easily placed in the ciliary sulcus 30 of eye 22. If any problems developed with the inserted lens 10, it can be very easily removed by reversing the hereintofore described process.

While in the foregoing embodiments of the present invention have been set forth in considerable detail for the purposes of making a complete disclosure of the invention, it may be apparent to those of skill in the art that numerous changes may be made in such detail without departing from the spirit and principles of the invention.

What is claimed is:

1. A corrective lens for the in-tact natural lens within the eye comprising:
   a. an optical body formed of material which is intended to be bio-compatable with the eye; and
   b. means for positioning said optical body within the eye adjacent the in-tact natural lens of the eye said positioning means including forming said optical body with a side complimentarily conforming to the shape of a side of the outer surface of the in-tact natural lens intended for placement of said optical body on and along the outer surface of the in-tact natural lens.

2. The corrective lens of claim 1 in which said means for positioning said optical body further comprises forming said optical body of flexible material.

3. The corrective lens of claim 1 in which said means for positioning said optical body further comprises at least one appendage connected to said optical body and of a length to extend the peripheral portion of the eye.

4. The corrective lens of claim 3 in which said at least one appendage is formed of flexible material.

5. The corrective lens of claim 3 in which said at least one appendage possesses a greater rigidity than said optical body.

6. The corrective lens of claim 4 in which said at least one appendage of flexible material includes reinforcing elements of rigid material relative to said flexible material of said at least one appendage.

7. The corrective lens of claim 6 which additionally comprises a haptic connected to said at least one appendage and said optical body.

8. The corrective lens of claim 1 in which said means for positioning said optical body within the eye adjacent the in-tact natural lens of the eye includes means for positioning said optical body within the posterior chamber of the eye.

* * * * *